United States Patent
Johnson et al.

(10) Patent No.: US 8,123,044 B2
(45) Date of Patent: Feb. 28, 2012

(54) ACTUATION OF PARALLEL MICROFLUIDIC ARRAYS

(75) Inventors: Andrew Johnson, Randolph, MA (US); John R. Gilbert, Brookline, MA (US); Manish Deshpande, Canton, MA (US); Hugh Lewis, Gravelotte (ZA); Bernard Bunner, Cambridge, MA (US)

(73) Assignee: Cytonome/ST, LLC, Boston, MA (US)

( * ) Notice: Subject to any disclaimer, the term of this patent is extended or adjusted under 35 U.S.C. 154(b) by 909 days.

(21) Appl. No.: 11/800,469

(22) Filed: May 4, 2007

(65) Prior Publication Data

US 2008/0087584 A1    Apr. 17, 2008

Related U.S. Application Data

(60) Provisional application No. 60/798,154, filed on May 5, 2006.

(51) Int. Cl.
*B07C 5/00* (2006.01)

(52) U.S. Cl. .......... 209/559; 209/552; 209/576; 422/73; 435/325

(58) Field of Classification Search .................. 209/552, 209/559, 576; 137/833; 222/135; 435/325; 422/73, 100, 102; 436/180
See application file for complete search history.

(56) References Cited

U.S. PATENT DOCUMENTS

| | | | |
|---|---|---|---|
| 5,837,200 A * | 11/1998 | Diessel et al. | 422/73 |
| 6,103,199 A | 8/2000 | Bjornson et al. | |
| 6,838,056 B2 * | 1/2005 | Foster | 422/504 |
| 7,157,274 B2 * | 1/2007 | Bohm et al. | 435/325 |
| 7,220,594 B2 * | 5/2007 | Foster et al. | 436/180 |
| 7,476,363 B2 * | 1/2009 | Unger et al. | 422/504 |
| 7,569,788 B2 * | 8/2009 | Deshpande et al. | 209/576 |
| 2002/0124896 A1 * | 9/2002 | O'Connor et al. | 137/833 |
| 2004/0050866 A1 | 3/2004 | Ingenhoven et al. | |
| 2005/0183995 A1 * | 8/2005 | Deshpande et al. | 209/552 |

FOREIGN PATENT DOCUMENTS

FR    2865145 A1    7/2005

OTHER PUBLICATIONS

Invitation to Pay Additional Fees for Application No. PCT/US2007/010959, dated Feb. 1, 2008.
International Search Report for Application No. PCT/US2007/010959, dated Aug. 8, 2008.

* cited by examiner

*Primary Examiner* — Terrell Matthews
(74) *Attorney, Agent, or Firm* — McCarter & English, LLP

(57) ABSTRACT

An improved actuator for use in a microfluidic particle sorting system utilizes a staggered packing scheme for a plurality of actuators used to selectively deflect a particle in an associated sorting channel from a stream of channels. An actuator block may be provided for housing a two-dimensional array of actuators, each configured to align with an actuation port in an associated sorting chip containing a plurality of sorting channels. The actuator block may include a built-in stressing means to pre-stress each actuator housed by the block. An actuator comprising a piezo-electric stack may employ contact-based electrical connection rather than soldered wires to improve packing density. The actuator may be an external actuator. That is, the external actuator is external to the substrate in which the sorting channels are formed.

37 Claims, 9 Drawing Sheets

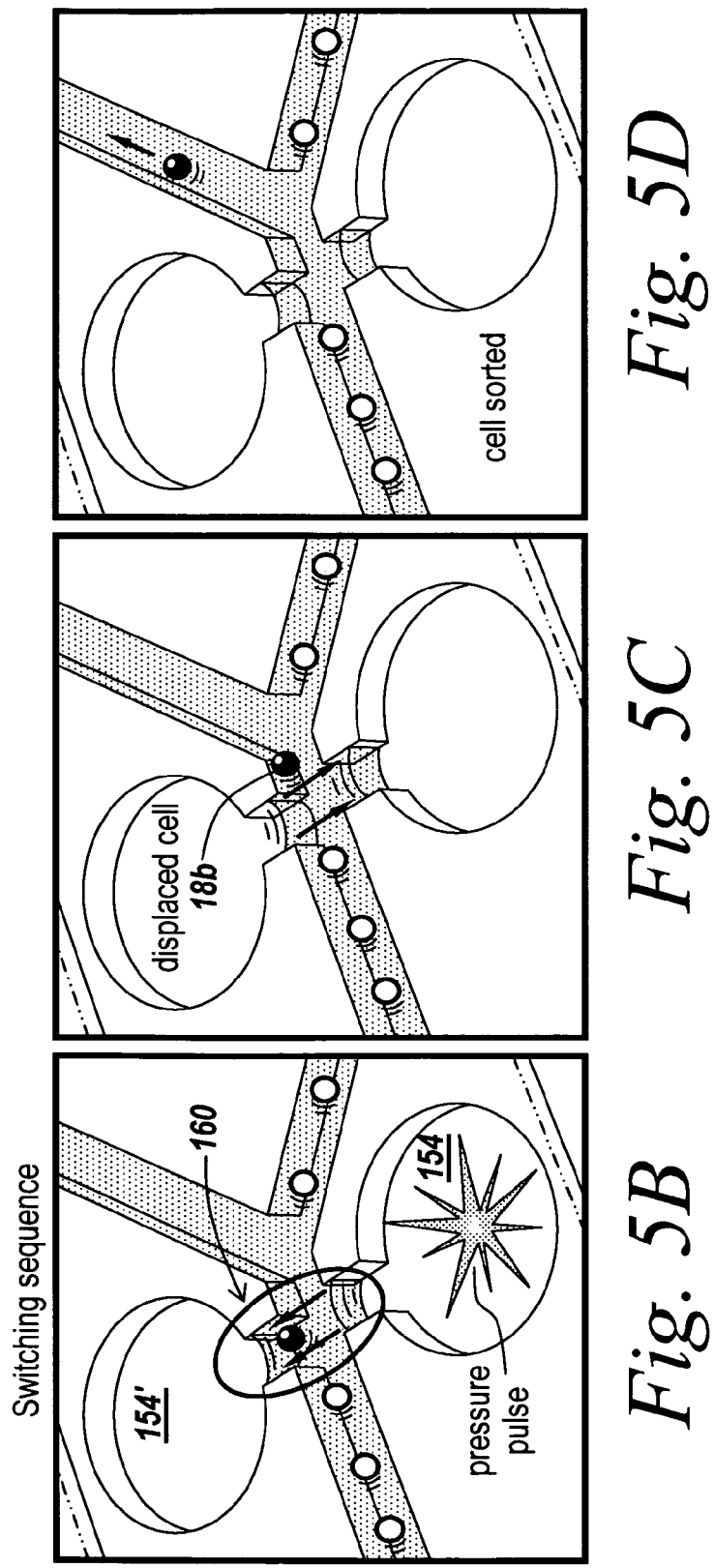

ACTUATION OF PARALLEL MICROFLUIDIC ARRAYS

RELATED APPLICATIONS

The present invention claims priority to U.S. Provisional Patent Application Ser. No. 60/798,154, filed May 5, 2006, and entitled "Actuation of Parallel Microfluidic Arrays", the contents of which are herein incorporated by reference.

FIELD OF THE INVENTION

The present invention relates to an actuator for use in a microfluidic particle processing system or device. In particular, the present invention relates to an actuator for use with a parallel array microfluidic sorting device for sorting particles in a plurality of parallel channels.

BACKGROUND

Microfluidic devices may be used in a variety of applications to perform any number of microfluidic processes on particles.

In the fields of biotechnology, and especially cytology and drug screening, there is a need for high throughput sorting of particles. Examples of particles that require sorting are various types of cells, such as blood platelets, white blood cells, tumorous cells, embryonic cells and the like. These particles are especially of interest in the field of cytology. Other particles are (macro) molecular species such as proteins, enzymes and poly-nucleotides. This family of particles is of particular interest in the field of drug screening during the development of new drugs.

Methods and apparatuses for particle sorting are known, and the majority described in the prior art work in the condition where the particles are suspended in a liquid flowing through a channel network having at least a branch point downstream and are operated according the detect-decide-deflect principle. The moving particle is first analyzed for a specific characteristic, such as optical absorption, fluorescent intensity, size, or another suitable characteristic. Depending on the outcome of this detection phase, it is decided how the particle will be further handled. The outcome of the decision is then applied to deflect the direction of specific particle towards a predetermined branch of the channel network.

Of importance is the throughput of the sorting apparatus, i.e. how many particles can be sorted per unit of time. Typical sorting rates for sorters employing flows of particle suspension in closed channels are in the range from a few hundred particles per second to thousands of particles per second, for a single sorting unit.

In certain microfluidic processes, such as particle sorting, certain actuators used to actuate a process, such as separation of particles having a predetermined characteristic from particles that do not have a predetermined characteristic, may present drawbacks. For example, certain actuators may take up a relatively large amount of space on a microfluidic chip, limiting the efficiency with which actuators can be packaged on the microfluidic chip, thereby also limiting the density or efficiency of packing of an array of parallel channels.

SUMMARY

The present invention provides an improved actuator for use in a microfluidic particle sorting system. In one embodiment, the present invention provides a staggered packing scheme for a plurality of actuators used to selectively deflect a particle in an associated sorting channel from a stream of channels. In another embodiment, an actuator block is provided for housing a two-dimensional array of actuators, each configured to align with an actuation port in an associated sorting chip containing a plurality of sorting channels. The actuator block may include a built-in stressing means to pre-stress each actuator housed by the block. In another embodiment, an actuator comprising a piezo-electric stack may employ contact-based electrical connection rather than soldered wires to improve packing density. In one embodiment, the actuator is an external actuator. That is, the external actuator is external to the substrate in which the sorting channels are formed.

According to one aspect of the invention, a system for sorting particles, comprises a microfluidic chip containing a plurality of microsorters, each microsorter having an actuation port for interfacing with a displacement actuator for selectively actuating the microsorter to deflect a particle having a predetermined characteristic from a stream of particles, wherein at least one of the actuation ports of a first microsorter is located in a different coordinate along the chip from an actuation port of a second microsorter and a block holding a plurality of displacement actuators such that the location of each actuator in the block corresponds to the location of an associated actuator ports in the microsorter chip when the block and chip are brought together.

According to another aspect of the invention, a system for providing dense arrays of displacement actuators comprises a block assembly that holds actuators for selectively activating an associated sorter in a fixed two-dimensional array, a layer in the block assembly which compresses each actuator against an independent flexing means to provide pre-stress and a plurality of actuation pins mounted in the block.

According to still another aspect of the invention, a displacement actuator device comprises a piezoelectric stack, an actuating pin for contact with a surface to be displaced connected to a first end of the piezoelectric stack, a mounting-pin for holding the mounting the displacement actuator device coupled to a second end of the piezoelectric stack and a conductive coating disposed over the mounting-pin and extending at least partially over the piezoelectric stack to provide an electrical connection to the piezoelectric stack.

BRIEF DESCRIPTION OF THE FIGURES

FIGS. 5a-5d illustrate another embodiment of the particle sorting module during sorting of a stream of particles based on a predetermined characteristic.

DETAILED DESCRIPTION

The present invention provides an improved actuation system for use in a microfluidic particle sorting system that sorts particles suspended in a liquid. The particle sorting system provides high-throughput, low error sorting of particles based on a predetermined characteristic. The present invention will be described below relative to illustrative embodiments. Those skilled in the art will appreciate that the present invention may be implemented in a number of different applications and embodiments and is not specifically limited in its application to the particular embodiments depicted herein.

Figure 1:
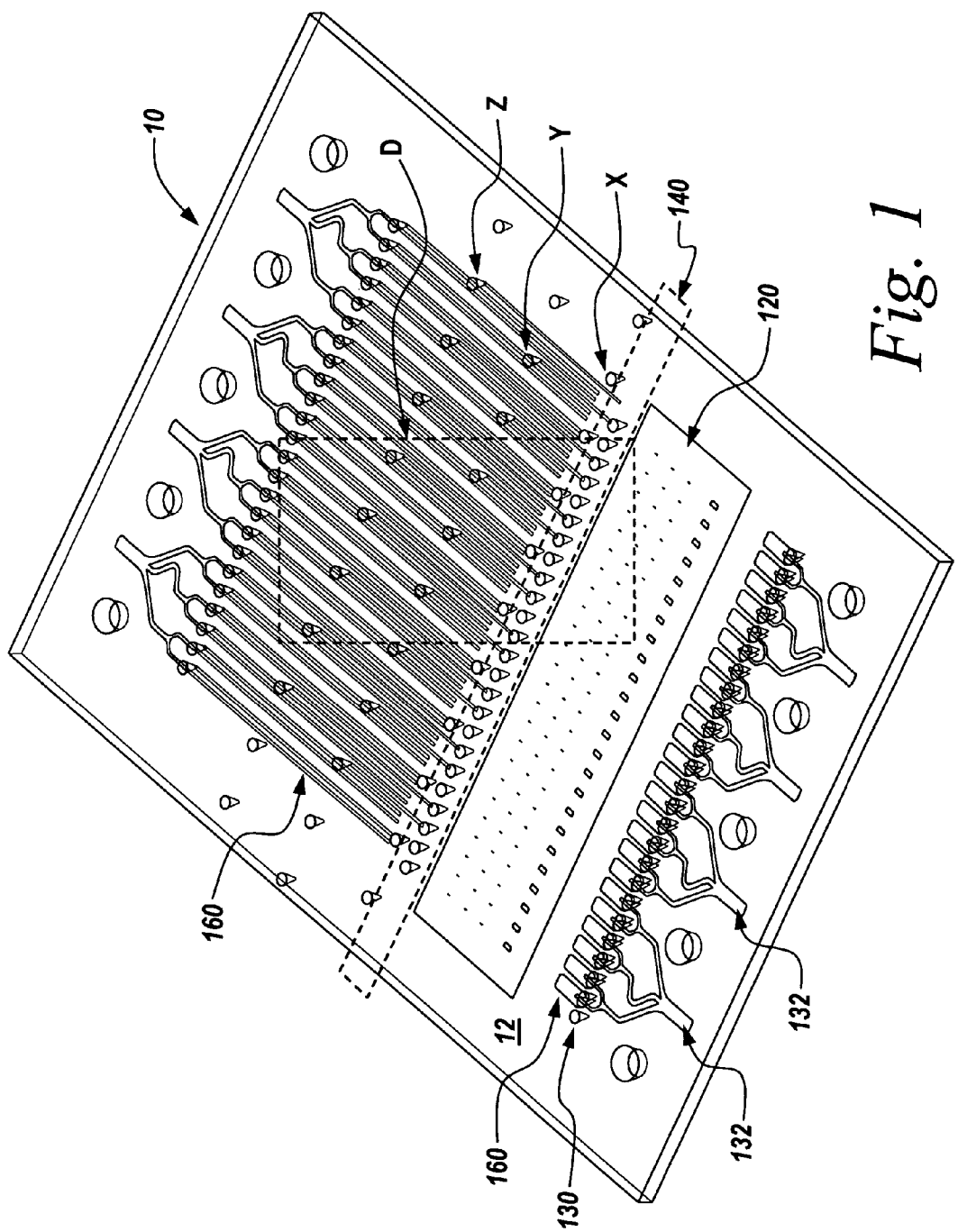
FIG. 1 illustrates a microfluidic particle sorting system according to an illustrative embodiment of the invention.

FIG. 1 illustrates a microfluidic particle processing system 10 according to an illustrative embodiment of the invention. The illustrative particle processing system comprises a particle sorting system for sorting particles flowing through a plurality of parallel channels based on one or more predetermined characteristics. The illustrative particle processing system 10 is formed on a substrate 12 and includes a number of processing channels, illustrated as sorting channels 160, for processing streams of an input sample in parallel. The processing system 10 includes a plurality of sample inlets 130 for inputting a sample to the system. In the illustrative embodiment, the sample inlets 130 intersect inlet channels 132, which flow a processing fluid, such as sheath fluid through the system. The sample inlets 130 and inlet channels 132 create a sheath flow carrying particles to be processed by the system through the parallel processing channels 160.

A suitable sheath flow system is described in U.S. patent application Ser. No. 10/979,848, filed Nov. 1, 2004, the contents of which are herein incorporated by reference. However, the invention is not limited to such a manner of inputting a sample and/or sheath flow to a particle processing system, and any suitable means may be used.

A detection region 120 receives the sheath flow containing the particles to be processed flowing through the parallel channels 110 and analyzes the particles. In the illustrative embodiment, the detection system observes the particles to identify particles having a predetermined characteristic. The detection region includes one or a plurality of detectors for sensing a predetermined characteristic in a target particle flowing through the channels 160.

A suitable detection system for analyzing particles is described in U.S. patent application Ser. No. 10/915,016, the contents of which are herein incorporated by reference. One skilled in the art will recognize that any suitable means of analyzing particles may be used.

In a processing region 140, the processing system 10 performs a selected process on the particles flowing through the channels 110. In the illustrative embodiment, the processing region contains a series 150 of switches for separating particles determined by detectors in the detection region 120 to have one or more predetermined characteristics from particles not having the predetermined characteristic.

Figure 2:
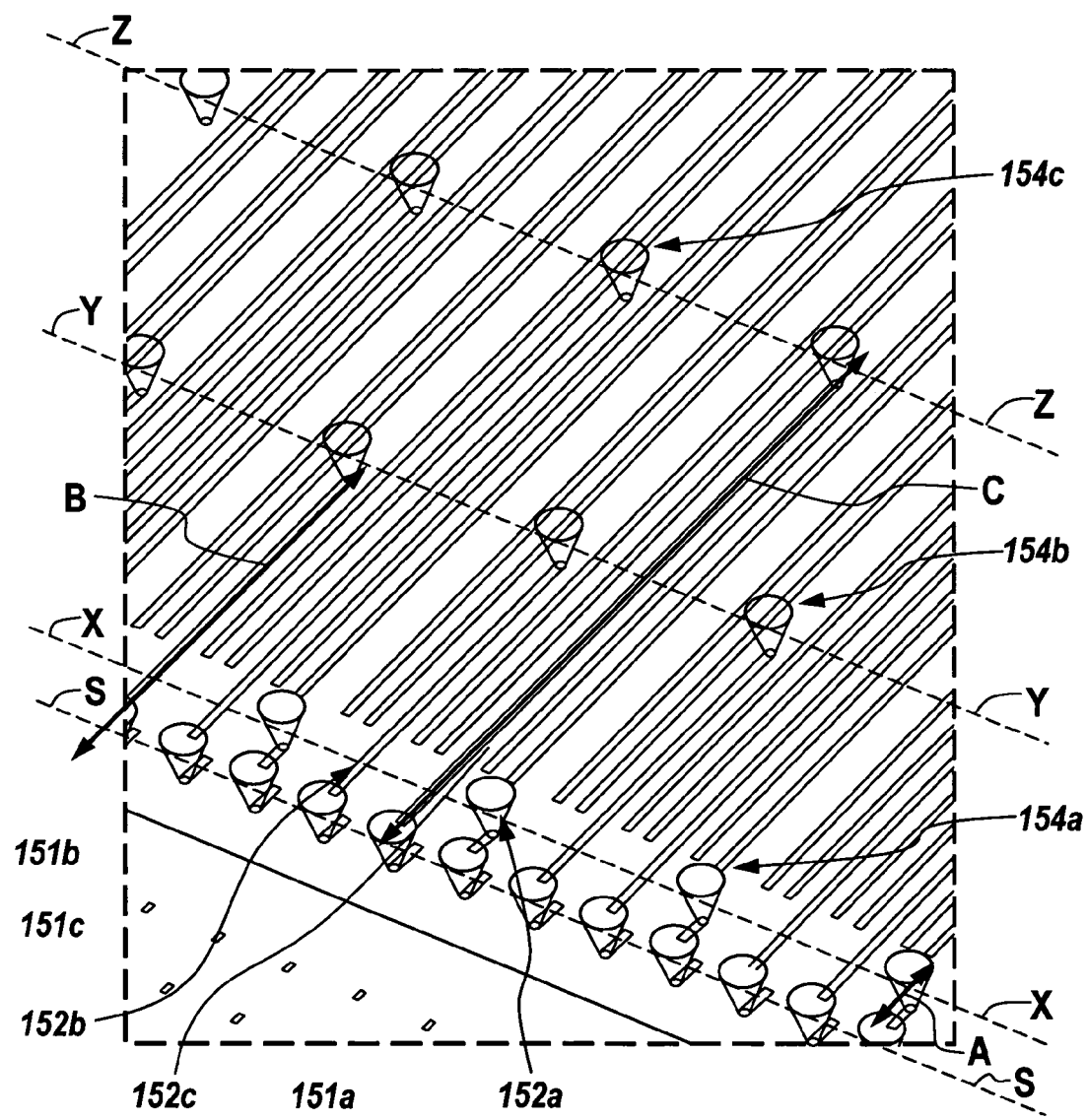
FIG. 2 is a detailed view of a region of the microfluidic particle sorting system of FIG. 1.

FIG. 2 is a detailed view of the region D in the particle processing system 10 of FIG. 1.

Figure 3:
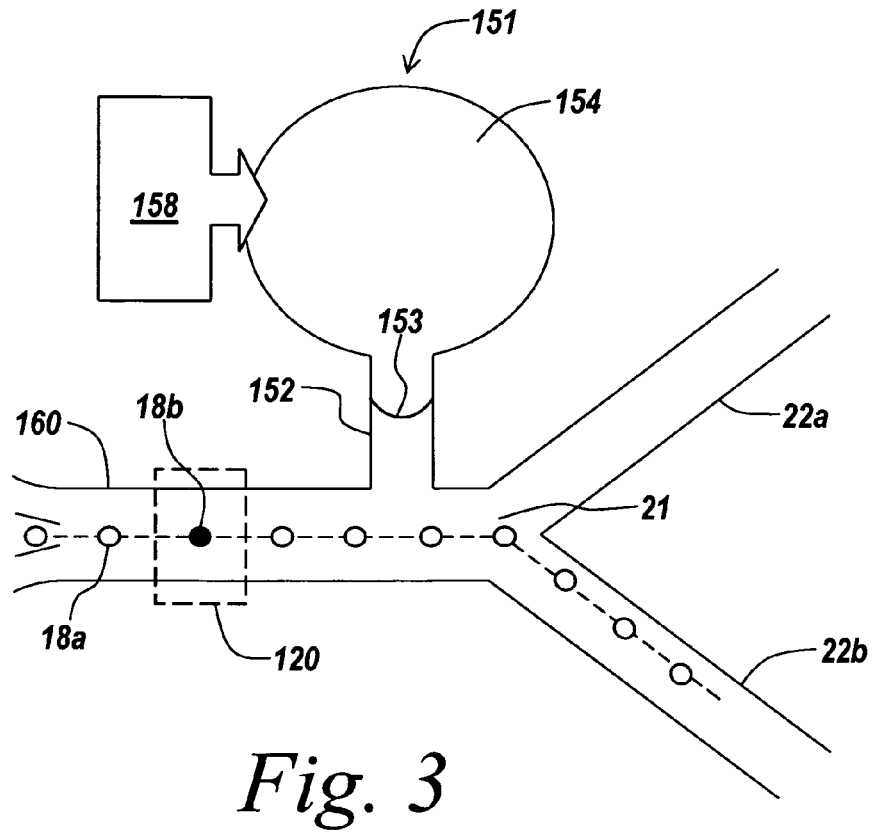
FIG. 3 illustrate a particle sorting module in the microfluidic particle sorting system according to one embodiment of the invention.

FIG. 3 illustrates a suitable switch 151 employed in the processing region of an illustrative embodiment of the invention. Each sorting channel 160 is associated with a dedicated switch 151 to perform sorting of particles within that channel. As shown, the sorting channel 160 conveys the particles suspended in the carrier liquid through the switching region. In the sorting region, the sorting channel 160 branches into a first branch 22a and a second branch 22b at a branch point 21. The illustrative switch 151 separates particles by selectively applying a pressure pulse to selected particles 18b in the channel 160 identified by the detection region 120 to deflect particles having the predetermined characteristic into a first outlet 22a of the channel, while particles 18a not having the predetermined characteristic flow into a second outlet 22b of the channel 160. The detection region 120 is defined in the sorting channel upstream of the switching region, and is associated with a detector, as described above, to sense a predetermined characteristic of particles in the detection region 20.

According to the illustrative embodiment, each switch 151 includes a side channel 152 intersecting the sorting channel 160 in the switching region. A fluid, such as the sheath fluid, partially fills the side channel 152 to form a meniscus 153 therein. The side channel 152 extends to and terminates in a sealed chamber 154, which is preferably filled with a fluid, such as air, other than the sheath fluid. The meniscus 153 interfaces and forms a barrier between the sheath fluid and the sealed chamber 154. The chamber 154 preferably includes a flexible or movable wall, which, when deflected or moved inwards, creates an increase in pressure in the sealed chamber 154. The chamber 154 serves as an actuation port to interface the sorting components formed on the substrate with an external actuator, as described below.

An actuator 158 is also provided for actuating the switch 151 when the detector in the detection region identifies a particle having a predetermined characteristic. In some embodiments, the actuator 158 is external to the switch 151. The actuator, when actuated, momentarily causes a flow disturbance in the sorting channel 160 to deflect the flow therein. The actuator 158 selectively increases the pressure in the chamber 154, causing the flow in the sorting channel near the side channel 152 to be displaced inwards, substantially perpendicular to the normal flow in the sorting channel 160. This transient liquid displacement, having a component perpendicular to the normal flow in the sorting, can be applied in deflecting particles having predetermined characteristics to separate them from the remaining particles in the mixture.

The actuator 158 is preferably a displacement actuator, as described below.

A buffer may optionally be provided for absorbing the pressure pulse created by the actuator.

Preferably, the actuator 158 is external to the substrate in which the sorting channels 160 are formed. The sealed chamber 154 may also be formed external to the substrate.

Figure 4:
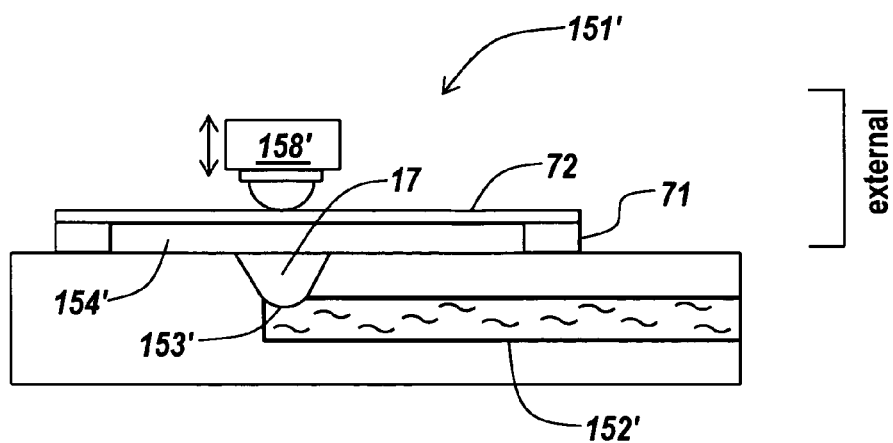
FIG. 4 illustrates another embodiment of a particle sorting module suitable for use in the particle sorting system of the invention.

FIG. 4 illustrates another embodiment of a switch suitable for creating a pressure pulse to separate particles of interest from other particles in a stream of particles and/or acting as a buffer for absorbing a pressure pulse according to the teachings of the present invention. As shown, the switch 151' is formed adjacent to a side passage 152' formed in a substrate 12 which leads to the sorting channel 160. The side passage 152' includes a fluid interface port 17 formed by an aperture in the side wall of the passage. A sealed compression chamber 154' is positioned adjacent to the side passage 152' and communicates with the side passage through the fluid interface port. The illustrative chamber 154' is formed by a seal 71 and a flexible membrane 72. The carrier fluid in the side passage 152' forms a meniscus 153' at the interface between the side passage and the chamber. The actuator 158' depresses the flexible membrane to increase the pressure in the chamber, which deflects the meniscus and causes a pressure pulse in the carrier fluid.

Figure 5A:
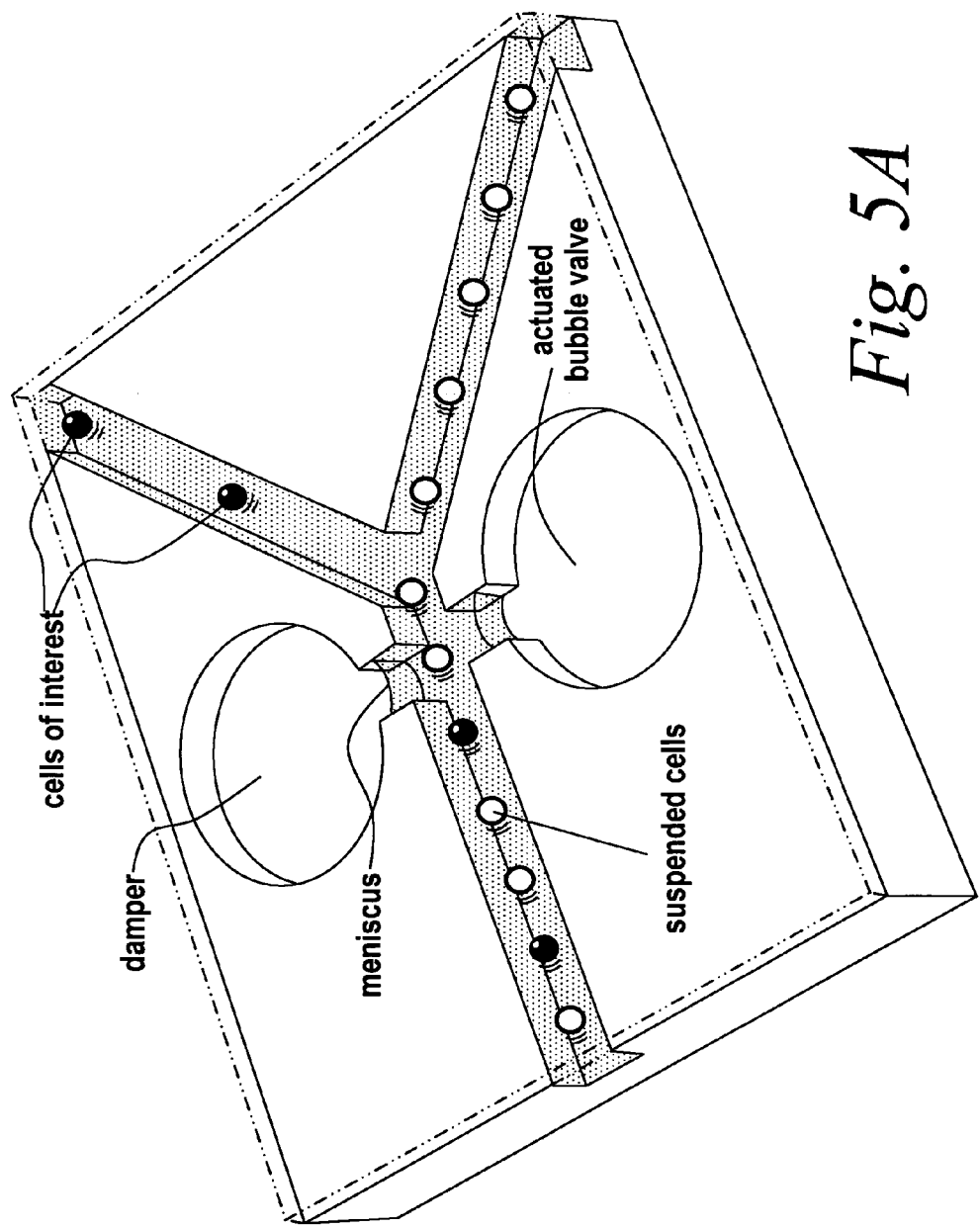

FIGS. 5a-5d illustrate the switching operation of switch 151 in the particle sorting system 10 of FIGS. 1-4. In the embodiment of FIGS. 5a-5d, the switch 151 includes a buffer for absorbing pressure pulses created when the actuator 158 increases the pressure in the chamber 154. The buffer includes a second side passage terminating in a sealed chamber 154' formed opposite the switch side passage 154. In FIG. 5A, a detector in the detection region 120 senses the predetermined characteristic in a particle and raises a signal to activate the actuator 158. Upon activation of the actuator, the pressure within the reservoir 154 of the switch 151 is increased, deflecting the meniscus 153 and causing a transient discharge of liquid from the first side passage 152, as indicated by the arrow in FIG. 5B. The sudden pressure increase caused at this point in the sorting channel causes liquid to flow into the second side passage forming the buffer, because of the resilient properties of the second reservoir buffer. This movement of liquid into the buffer side passage is indicated with an arrow. As a result, as can be seen in FIG. 5C, the flow through the sorting channel is deflected, causing the selected particle of interest 18b located between the first side passage 154 and the buffer side passage to be shifted perpendicular to its flow direction in the normal state. The deflected particle of interest, displaced radially by the pressure pulse, then flows into the first outlet channel 22a, while unselected particles, unaffected by the pressure pulse, flow into the second outlet channel 22b, thereby separating particles having the predetermined characteristic from particles not having the predetermined characteristic, as shown in FIGS. 5A and 5D.

When the actuator 158 is deactivated, the pressure inside the reservoirs 154, 154' returns to the normal pressure, allowing for normal flow of particles into the second outlet channel 22b.

This process of detecting and selective deflecting of particles may be repeated many times per second for sorting particles at a high rate. Adopting the fluid switching as described, switching operations may be executed up to around several thousand switching operations per second, yielding sorting rates in the order of million sorted particles per hour.

A suitable switching mechanism is described in U.S. Pat. Nos. 6,877,528, 6,808,075, 6,976,590 and 7,157,274 and U.S. patent application Ser. No. 11/295,183 the contents of which are herein incorporated by reference.

According to an illustrative embodiment of the invention, as shown in FIGS. 1 and 2 the actuators 158 for the array of sorting channels 160 are staggered on the microfluidic substrate 12 to allow dense packing of the channels on the substrate 12. For example, in the illustrative embodiment, the switching regions of the switches, where the side channels 152 intersect the sorting channels 160 in each switch, may be spaced substantially equally in region 140. The side channels 152 of the switches may have varying lengths to allow the location of the actuators 158 at the end of the side channels 152 to be staggered. Nevertheless in other embodiments of the present invention, the switches in the switching region can be staggered. Staggering the switches requires compensation for different times from detection to actuation (for each length) and possibly compensation for flow resistance matching to allow for the fact that the resistance in the sorted and unsorted channels (the y-channels post switching joint) would not all be intrinsically matched.

In the illustrative embodiment, the actuators 158 are staggered at different coordinates along the substrate in intervals of three. As used herein, the term "coordinate" refers to a longitudinal position of an element along a substrate. For example, the term coordinate may refer to the distance of an actuator and/or actuator port from a row of switches, or another row parallel to a front (input) end or back (output) end of the substrate. In this embodiment the actuation ports are staggered on chip by using asymmetric actuator port arm lengths while leaving the location of the switching joints in a line S. For example, the actuators 158 may be staggered by selectively extending the side channels of the switches to locate the actuator port and chamber 154 at staggered distances from the switching region. For example, in the illustrative embodiment shown in FIGS. 1 and 2, the channels are groups in subsets of threes. A first side channel 152a of a first switch 151a in a series of three switches has a first length A, terminating in a sealed chamber 154a forming an actuator port at line X, such that the corresponding actuator is located along line X. A second side channel 152b of a second switch 151b has a second length B, terminating in a sealed chamber 154b forming an actuator port at line Y, such that the corresponding actuator is located along line Y. A third side channel 152c of a third switch 151c has a third length C, terminating in a sealed chamber 154c forming an actuator port at line Z, such that the corresponding actuator is located along line Z, which is furthest from the switching regions, which are aligned along line S. Thus, every third actuator and associated chamber aligns along the same coordinate of the substrate (i.e., the same row). In this manner, one third of the actuators for the series of sorting channels and switches are located along line X, closest to switching line S, a second third of the actuators are located along line Y, farther from the switching line S, and the last third of the actuators are located along line Z, farthest from the switching line S.

The illustrative packing scheme thus enables dense packing of the sorting channels. In one embodiment, the sorting channels may be packed with a spacing between channels at as little as 900 microns. In contrast, were the actuators to align along the same line, more space would be required.

By using staggering actuation ports in every third channels the illustrative embodiment of the invention enables conventional piezo stacks or electroconstrictive or other type of displacement actuator that are generally too large to pack linearly.

Although the array of actuators and the corresponding actuation ports of the microfluidic particle processing system are illustrated with three staggered rows, those skilled in the art will appreciate that the array of actuators and the corresponding actuation ports of the microfluidic particle processing system of the present invention can have fewer rows, for example, two rows, or more than three rows, for example, four rows, five rows, six rows and so on.

Alternatively, the switching points in region 140 may also or alternatively be staggered, so that line S comprises several staggered lines.

In this embodiment, the actuator array and the actuator port array are designed to match spacing and reach a new minimum interchannel spacing.

Figure 6:
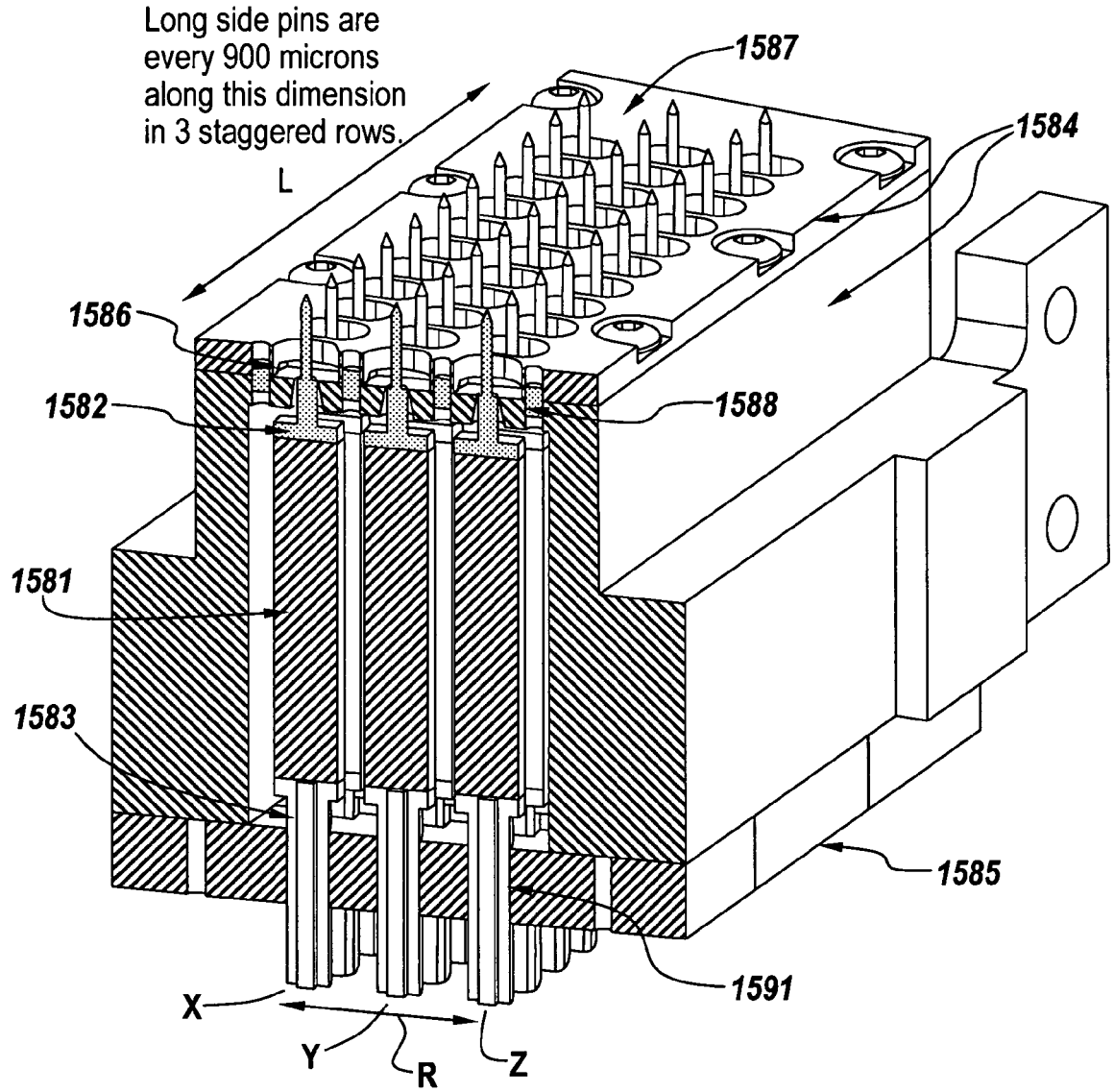
FIG. 6 illustrates an embodiment of an actuator block for housing a plurality of external actuators used with the particle sorting system of FIG. 1 in a two-dimensional array.

According to another embodiment of the invention, the particle processing system may include a self-aligning actuator packing block containing a plurality of actuators for actuating a plurality of switches in the particle processing system. FIG. 6 illustrates an embodiment of a self-aligning actuator packing block 400 suitable for actuating switches when a detection system 120 detects a predetermined characteristic in a particle in a sorting channel 160. When coupled to the substrate 12, each actuator 158 in the block aligns with a sealed chamber at the termination of a switching side channel to associate the actuator with a selected switch and sorting channel 160. A controller selectively actuates the appropriate actuator 158 in the block when signaled by the detection system 120 to increase pressure in an associated switching chamber, causing deflecting of a meniscus in an associated switching side channel to deflect a targeted particle in the associated sorting channel. The actuator block 400 may actuate one, a plurality or all of the actuators at once, if appropriate.

The illustrative actuators include built-in pre-stressed springs, flexures or other suitable flexible devices for each actuator, such as for each actuator pin.

In the illustrative embodiment, a plurality of actuators 158 are densely packed in a two-dimensional array. Each illustrative actuator 158 includes a piezoelectric stack 1581, or other suitable displacement actuator that expands or retracts when supplied with a particular signal. Alternatively, the piezoelectric stack may comprise an electroconstrictive displacement actuator known in the art. An actuation pin 1582, or other suitable device, is mounted through any suitable means to the front side of the piezoelectric stack. The actuation pin 1582 may be mounted to the piezoelectric stack through any suitable means, including glue, cement or other bonding means. A mounting pin 1583 is mounted on the back of each piezoelectric stack 1581. The actuation pin 1582 is configured to extend from the block 400 and contact a movable wall of a sealed switching chamber when the piezoelectric stack expands to create the necessary pressure pulse to selectively deflect a targeted particle in an associated sorting channel. Together, the stacked actuation pin 1582, piezo stack 1581 and mounting pin 1583 forms a "piezo pin" unit.

The block for housing the array of piezo pins includes a back plate 1585, into which the piezo pins may be fixed. The piezo pins are preferably fixed to the back plate 1585, such that the mounting pins 1583 extend through apertures 1591 formed in the back plate. The mounting pins 1583 may conduct electricity from a source to actuate the actuator. After fixing the piezo pins, the back plate is then mounted into a front block 1584 so that the piezo pins are compressed against flexures 1586 located in the top 1587 of the front block 1584. Any suitable device may be used to provide compression of the piezo pins and the invention is not limited to the illustrative flexures 1586. The top 1587 of the front block 1584 faces the substrate 12 of the sorting system when the block is coupled to the substrate. The tips of the piezo pins, formed by the actuation pins 1582, protrude through apertures 1588 in the front block so that they may contact the actuation ports of the microsorter system without mechanical interference between the substrate 12 and the actuator block system 400.

In the illustrative embodiment, the actuator block 400 include three rows of piezo pins, shown along axis R. Each row corresponds to one of the lines X, Y and Z along which the sealed chambers at the termination of the side channels for each switch in the array of switches on the substrate are formed. In each row, the actuators are spaced along the length L of the actuator block so as to align with each sealed chamber in the subset of switches disposed along the associated line X, Y or Z. While the illustrative embodiment shows a staggering at intervals of three, one skilled in the art will recognize that the actuator side channels and associated actuators may be staggered at any suitable interval. For example, for alternate staggering, two rows of actuators would be formed in the block. The number of rows in the actuator block corresponds to the number of subsets of switches in which the staggering occurs.

The illustrative actuator block 400 implements implement a dense packing array to conserve space. In the illustrative embodiment, each actuator, i.e., piezo pin, or other suitable displacement actuator, is spaced at less than about 4 mm spacing between actuator centers, such that the actuation pins are found linearly at less than 2 mm intervals along the long side of the block and preferably less than 1 mm.

In the illustrative embodiment, the flexures 1586 are provided to maintain the actuators in a pre-stressed state to promote reliable piezoelectric stack operation over long times and many cycles. In the resting position (zero voltage applied in one embodiment) the piezo pins or other actuation devices are held in compression. When a voltage is applied to the mounting pin, the mounting pin 1583 transmits the voltage to the piezoelectric stack 1581 to expand the actuator against the compressive pressure, thereby actuating the associated switch 151.

Figure 7:
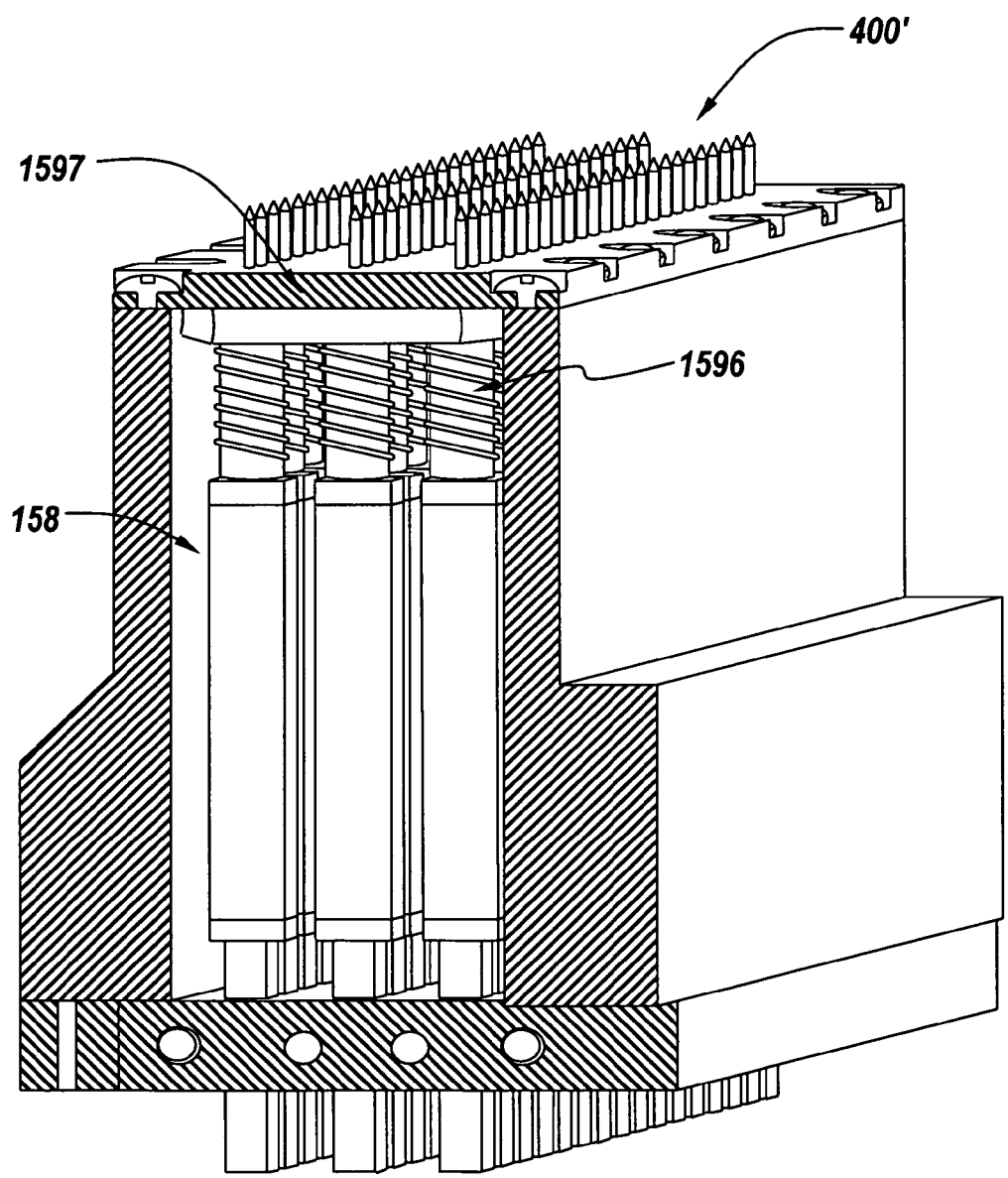
FIG. 7 illustrates another embodiment of the actuator block.

According to another embodiment of the invention, shown in FIG. 7, an actuator block 400' for a particle processing system may employ helical springs 1596 to compress the displacement actuation device, such as a piezo pin, in a resting position to provide built-in pre-stress. A helical spring 1596 may be placed over each piezo pin 158 or other actuation device. The spring loaded piezo pins may then be compressed all together against a rigid surface 1597, which is located in the top of the actuator block 400' in the illustrative embodiment. The rigid surface 1597 may be located in any suitable location.

Referring to FIGS. 8-11*d*, the present invention may also or alternatively provide enhanced performance by providing the piezo-pin actuator with a contact based electrical connection, rather than employing soldered or crimped wires, thereby further improving packing density.

Piezo-stacks conventionally have wires soldered to the electrodes on opposite sides of the stack. In any dense packing implementation those wires would have to be brought out of the block and connected one at a time to the piezo driver electronics. In the illustrative electronic pin 158, the sides of the mounting pin 1583 at the back of the piezo-pin structure are coated with a coating 1593 (or metallized or have conductors mounted) with conducting material, such as metal, for example copper, which is extended over the sides of the piezo stack 1581 itself to allow the designer to use conductive springs 1594 mounted in or below the acutator block back plate to make electrical connection by insertion, similar to a integrated circuit chip in-line package pin socket.

The integrated conductor surfaces on the illustrative piezo stack based pins (piezo-pins) enable electrical connections to be made using conductive springs—enabling insertion connections instead of soldered ones.

Figure 8:
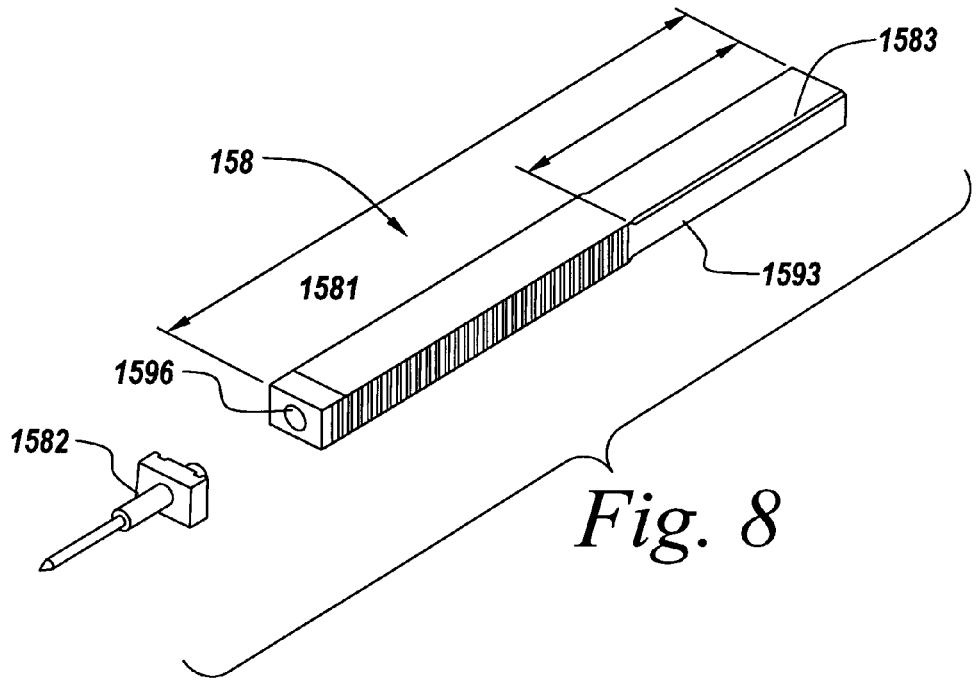
FIG. 8 illustrates an embodiment of an actuator used to selectively actuate a sorting switch in the particle sorting system of FIG. 1.
Figure 9:
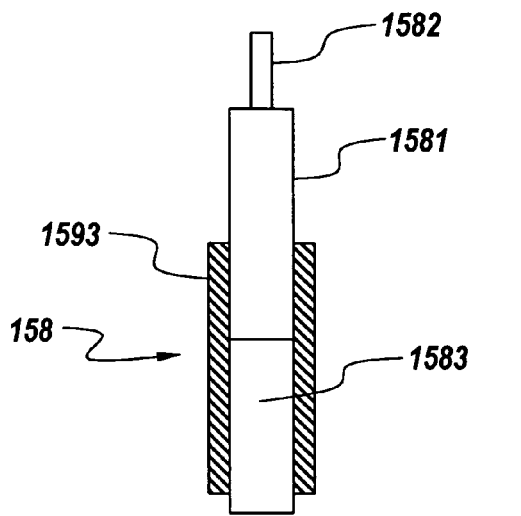
FIG. 9 illustrates another embodiment of the actuator.
Figure 10:
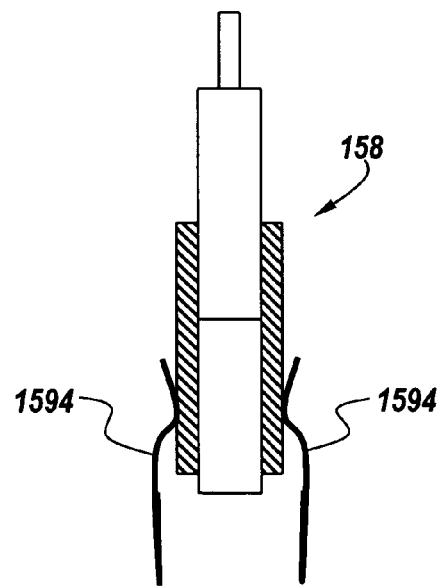
FIG. 10 illustrates the actuator of FIG. 9 including contact springs to provide an electrical connection to the actuator.
Figure 11A:
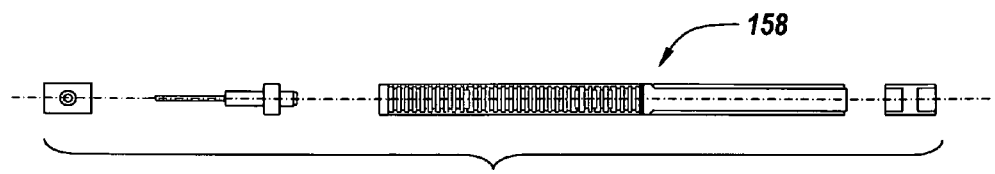
FIGS. 11A-11D illustrate the actuator of FIG. 8.
Figure 11B:
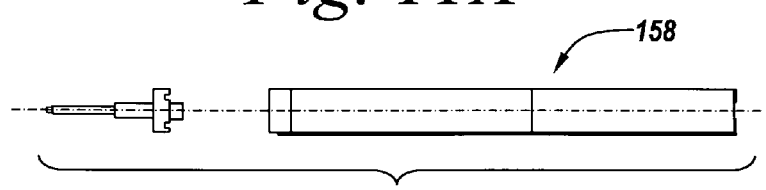
Figure 11C:
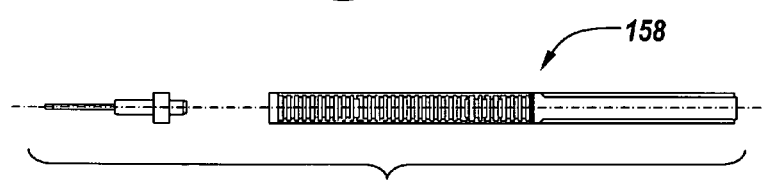
Figure 11D:
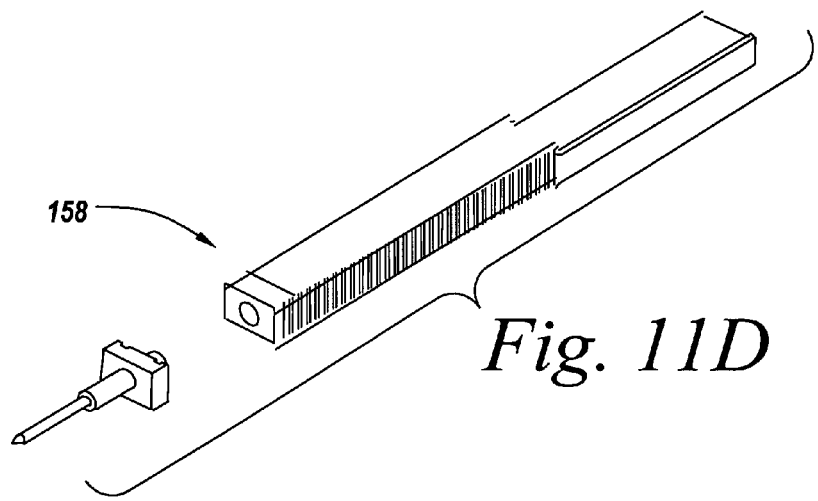

As shown in FIG. 8, the actuation pin 1582 may be mounted to the piezo stack 1581 using a protrusion on the back end of the actuation pin that is received by a recess 1598 in the front end of the piezo stack 1581. Any suitable mounting means may be used.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and protected by Letters Patent is:

1. A system for sorting particles, comprising:
   a microfluidic chip containing a plurality of microsorters, each microsorter having an actuation port for interfacing with a displacement actuator for selectively actuating the microsorter to deflect a particle having a predetermined characteristic from a stream of particles, wherein at least one of the actuation ports of a first microsorter is located in a different coordinate along the chip from an actuation port of a second microsorter;

an external actuator packing block holding a plurality of displacement actuators and a plurality of actuation devices such that the location of each actuation device in the block corresponds to the location of an associated actuator port in the microsorter chip when the block and chip are brought together, wherein each of the plurality of displacement actuators is formed by a plurality of piezo-electric elements in a stacked relationship and each of the plurality of displacement actuators is coupled to a respective one of the plurality of actuation devices; and an electric connector mounted to each stack of piezo-electric elements.

2. The system of claim 1, wherein the block provides pre-compression of each displacement actuator in an unexcited state.

3. The system of claim 1, wherein the displacement actuators each include an electroconstrictive displacement actuator.

4. The system of claim 1, wherein the actuation ports and displacement actuators are formed in an array having at least two rows.

5. The system of claim 1, wherein the actuation ports and displacement actuators are formed in an array having three rows.

6. The system of claim 1, wherein each microsorter comprises a branching switching region including a main sorting channel and two outlet channels, and an actuator port arm extending from the main sorting channel and terminating in the actuator port.

7. The system of claim 6, wherein a length of the actuator port arm of the first microsorter is different from a length of the actuator port arm of the second microsorter.

8. The system of claim 6, wherein the branched switching regions of the plurality of microsorters are aligned in a horizontal direction on the substrate.

9. The system of claim 1, wherein each actuator port comprises a sealed chamber.

10. The system of claim 1, wherein the actuator packing block includes a layer in the block assembly which compresses each actuator against an independent flexing means to provide pre-stress.

11. The system of claim 1, wherein the displacement actuators are held in a fixed two-dimensional array having at least two rows.

12. The system of claim 11, wherein the displacement actuators are held in an array having three rows.

13. The system of claim 10, wherein the flexing means comprises a helical spring.

14. The system of claim 10, wherein the flexing means comprises a flexure.

15. The system of claim 1, wherein each electric connector includes:
   a mounting-pin coupled to the piezo-electric stack; and
   a conductive coating disposed over the mounting-pin and extending at least partially over the piezo-electric stack to provide an electrical connection to the piezo-electric stack.

16. The system of claim 15 further comprising a socket containing conductive spring-loaded contacts into which the mounting-pin can be inserted such that its insertion into the socket provides electrical contact to the piezo-electric stack.

17. The system of claim 1, wherein the actuator packing block includes a back plate, wherein the actuators are fixed to the back plate.

18. The system of claim 17, wherein the actuator packing block further includes a front block mounted to the back plate.

19. The system of claim 18, wherein the mounting of the front block to the back plate compresses the actuators.

20. The system of claim 19, wherein each actuator is compressed against a flexible member.

21. The system of claim 1, wherein each actuator is further coupled to a mounting-pin.

22. The system of claim 21, wherein each mounting pin extends through an aperture formed in a back plate of the actuator packing block.

23. The system of claim 21, wherein each mounting-pin conducts electricity from a power source to actuate the stack of piezo-electric elements.

24. The system of claim 1, wherein each actuation device protrudes through an aperture in a front block of the actuator packing block.

25. The system of claim 1, wherein the plurality of actuators are arraigned in a staggered relationship.

26. The system of claim 1, wherein the actuation devices are actuation pins.

27. A system for sorting particles, comprising:
   a microfluidic chip containing a plurality of microsorters, each microsorter having an actuation port for interfacing with a displacement actuator for selectively actuating the microsorter to deflect a particle having a predetermined characteristic from a stream of particles, wherein at least one of the actuation ports of a first microsorter is located in a different coordinate along the chip from an actuation port of a second microsorter;
   an external actuator packing block holding a plurality of displacement actuators and a plurality of actuation devices such that the location of each actuation device in the block corresponds to the location of an associated actuator port in the microsorter chip when the block and chip are brought together;
   wherein each of the plurality of displacement actuators is formed by a plurality of piezo-electric elements in a stacked relationship and each of the plurality of displacement actuators is coupled to a respective one of the plurality of actuation devices; and
   wherein each actuation device protrudes through an aperture in a first portion of the actuator packing block.

28. The system of claim 27, wherein the block provides pre-compression of each displacement actuator in an unexcited state.

29. The system of claim 27, wherein the actuator packing block includes a layer in the block assembly which compresses each actuator against an independent flexing means to provide pre-stress.

30. The system of claim 29, wherein the flexing means comprises a helical spring.

31. The system of claim 29, wherein the flexing means comprises a flexure.

32. The system of claim 27, wherein the actuator packing block includes a back plate, wherein the actuators are fixed to the back plate.

33. The system of claim 32, wherein the first portion is mounted to the back plate and the mounting of the first portion to the back plate compresses the actuators.

34. The system of claim 27, wherein each actuator is compressed against a flexible member.

35. The system of claim 27, wherein each actuator is further coupled to a mounting-pin.

36. The system of claim 35, wherein each mounting pin extends through an aperture formed in a back plate of the actuator packing block.

37. The system of claim 35, wherein each mounting-pin conducts electricity from a power source to actuate the stack of piezo-electric elements.

* * * * *